United States Patent
Shimizu et al.

(10) Patent No.: US 7,920,732 B2
(45) Date of Patent: Apr. 5, 2011

(54) CAPSULE ENDOSCOPE SYSTEM AND ENDOSCOPIC IMAGE FILING METHOD

(75) Inventors: Kunimasa Shimizu, Minato-ku (JP);
Naoto Kinjo, Ashigarakami-gun (JP);
Kazumi Koike, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 123 days.

(21) Appl. No.: 12/370,078

(22) Filed: Feb. 12, 2009

(65) Prior Publication Data

US 2009/0203964 A1    Aug. 13, 2009

(30) Foreign Application Priority Data

Feb. 13, 2008    (JP) .................................. 2008-031719

(51) Int. Cl.
*G06K 9/00* (2006.01)

(52) U.S. Cl. ............ 382/128; 382/232; 348/45; 348/65; 348/72; 375/240; 600/101

(58) Field of Classification Search .................... 382/128
See application file for complete search history.

(56) References Cited

U.S. PATENT DOCUMENTS

| 6,709,387 | B1 * | 3/2004 | Glukhovsky et al. | 600/109 |
| 2003/0043263 | A1 * | 3/2003 | Glukhovsky et al. | 348/61 |
| 2003/0151661 | A1 * | 8/2003 | Davidson et al. | 348/65 |
| 2005/0025368 | A1 * | 2/2005 | Glukhovsky | 382/236 |
| 2005/0159643 | A1 * | 7/2005 | Zinaty et al. | 600/109 |
| 2006/0189843 | A1 * | 8/2006 | Nakamura et al. | 600/118 |
| 2009/0203964 | A1 * | 8/2009 | Shimizu et al. | 600/109 |

FOREIGN PATENT DOCUMENTS

JP    2005-124965 A    5/2005
JP    2007-236700 A    9/2007

* cited by examiner

*Primary Examiner* — Sath V Perungavoor
(74) *Attorney, Agent, or Firm* — Sughrue Mion, PLLC

(57) ABSTRACT

A capsule endoscope system includes a capsule endoscope, swallowable in a body, for forming an image. A receiver is positioned on the body, for wirelessly receiving the image from the capsule endoscope, to store the image. A workstation as information manager operates for image filing of the image from the receiver. A first wireless interface is incorporated in the receiver, for wirelessly transmitting the image during imaging with the capsule endoscope. A second wireless interface is positioned on the workstation, for wirelessly receiving the image from the first wireless interface. Furthermore, an image selector selects the image for image filing in the workstation among plural images received by the receiver. The first wireless interface transmits the selected image to the workstation. The receiver includes an image compressor for reducing a data size of the image received from the capsule endoscope before transmission in the first wireless interface.

12 Claims, 9 Drawing Sheets

CAPSULE ENDOSCOPE SYSTEM AND ENDOSCOPIC IMAGE FILING METHOD

BACKGROUND OF THE INVENTION

1. Field of the Invention

The present invention relates to a capsule endoscope system and endoscopic image filing method. More particularly, the present invention relates to a capsule endoscope system and endoscopic image filing method in which image reading of endoscopic images can be carried out with high efficiency.

2. Description Related to the Prior Art

A capsule endoscope has been recently developed for the purpose of medical examination of a patient's body. The capsule endoscope includes a capsule body of a very small size, and an image pickup device and a light source incorporated in the capsule body. For the examination, at first a patient orally swallows the capsule endoscope. The light source illuminates a body part in a gastrointestinal tract of his or her human body. The image pickup device creates an image of the body part. Image data are obtained. A receiver wirelessly receives a radio wave of the image data, and writes the image data in an internal flash memory as data storage.

After endoscopic imaging for examination, the receiver becomes connected with an information manager, such as a workstation, with a USB cable or the like. Image data from the receiver are entirely retrieved in the information manager. See U.S. Pat. Pub. No. 2006/189843 (corresponding to JP-A 2005-124965) and JP-A 2007-236700. A doctor or physician causes a monitor display panel to display endoscopic images according to the image data retrieved in the information manager, and observes those for diagnosis of the patient's body.

According to the techniques disclosed in those documents, the image reading cannot be started until the end of the examination, because image data from the capsule endoscope are stored in the receiver at first, and are retrieved in an information manager after the examination. There is a problem in that treatment according to a result of the diagnosis cannot be rapid, as considerably long time is required for the diagnosis.

SUMMARY OF THE INVENTION

In view of the foregoing problems, an object of the present invention is to provide a capsule endoscope system and endoscopic image filing method in which image reading of endoscopic images can be carried out with high efficiency.

In order to achieve the above and other objects and advantages of this invention, a capsule endoscope system includes a capsule endoscope, swallowable in a body, for forming an image in the body. A receiver is positioned on the body, for wirelessly receiving the image from the capsule endoscope, to store the image. An information manager files the image from the receiver, manages the image, and controls display of the image. A first wireless interface is positioned on the receiver, for wirelessly transmitting the image during imaging with the capsule endoscope. A second wireless interface is positioned on the information manager, for wirelessly receiving the image from the first wireless interface.

Furthermore, an image selector selects the image for image filing in the information manager among plural images received by the receiver. The first wireless interface transmits the selected image to the information manager.

The image selector is positioned on at least one of the receiver and the information manager.

The image selector determines similarity degree between two images among plural images received from the capsule endoscope by the receiver, and if the similarity degree is equal to or more than a predetermined threshold value, selects one of the two images, and if the similarity degree is less than the threshold value, selects the two images.

Furthermore, a memory is provided in one of the receiver and the information manager provided with the image selector, for storing a sample image feature value of a sample image. The image selector extracts an image feature value from the image obtained by the capsule endoscope, and determines similarity degree between the image and the sample image by comparing the image feature value with the sample image feature value, wherein if the similarity degree is equal to or more than a predetermined threshold value, the image is selected as detected to correspond to the sample image.

The memory stores the sample image feature value in association with lesion type information of a type of a lesion. Furthermore, an input interface inputs the lesion type information. The image selector reads the sample image feature value for comparison according to the input lesion type information.

The image selector is incorporated in the receiver.

In a preferred embodiment, the image selector is incorporated in the information manager.

The receiver includes a data size reduction device for reducing a data size of the image received from the capsule endoscope before transmission in the first wireless interface.

The second wireless interface transmits image selection information output by the image selector to the receiver. The receiver designates the image according to the image selection information from the second wireless interface, and transmits the designated image with the first wireless interface.

When there is a remaining image unselected with the image selector, the receiver abandons the remaining image or stores the remaining image in a modified form with a reduced size of data.

Also, an endoscopic image filing method of filing an image formed in a body with a capsule endoscope swallowed in the body is provided. In the endoscopic image filing method, the image is wirelessly received from the capsule endoscope to a receiver positioned on the body, to store the image. The image is wirelessly transmitted from the receiver during imaging with the capsule endoscope. The image wirelessly transmitted from the receiver is filed.

Furthermore, there is a step of selecting the image for image filing in the filing step among plural images received by the receiver. In the transmitting step, the selected image is transmitted.

The selecting step is carried out in at least one of the receiver and an information manager for the filing step.

In the selecting step, similarity degree between two images is determined among plural images received from the capsule endoscope by the receiver, and if the similarity degree is equal to or more than a predetermined threshold value, one of the two images is selected, and if the similarity degree is less than the threshold value, the two images are selected.

A sample image feature value of a sample image is predetermined. The selecting step includes extracting an image feature value from the image obtained by the capsule endoscope. Similarity degree between the image and the sample image is determined by comparing the image feature value with the sample image feature value, wherein if the similarity degree is equal to or more than a predetermined threshold value, the image is selected as detected to correspond to the sample image.

The sample image feature value is predetermined in association with lesion type information of a type of a lesion. Furthermore, the lesion type information is inputted. In the selecting step, the sample image feature value is read for comparison according to the input lesion type information.

The selecting step is carried out in the receiver.

In a preferred embodiment, the selecting step is carried out in the information manager.

Furthermore, a data size of the image received from the capsule endoscope to the receiver is reduced before the transmitting step.

Furthermore, there is an information transmitting step of transmitting image selection information output by the selecting step to the receiver. The receiver designates the image according to the image selection information from the information transmitting step, and transmits the designated image in the transmitting step.

When there is a remaining image unselected with the selecting step, the receiver abandons the remaining image or stores the remaining image in a modified form with a reduced size of data.

Also, a computer executable program for image filing of an image formed in a body with a capsule endoscope swallowed in said body is provided, and includes a program code for wirelessly receiving said image from said capsule endoscope to a receiver positioned on said body, to store said image. A program code is for wirelessly transmitting said image from said receiver during imaging with said capsule endoscope, to file said image wirelessly transmitted from said receiver.

Also, a user interface for image filing of an image formed in a body with a capsule endoscope swallowed in said body is provided, and includes a region for wirelessly receiving said image from said capsule endoscope to a receiver positioned on said body, to store said image. A region is for wirelessly transmitting said image from said receiver during imaging with said capsule endoscope, to file said image wirelessly transmitted from said receiver.

Consequently, image reading of endoscopic images can be carried out with high efficiency, because an image is wirelessly transmitted from the receiver toward an information manager for image filing during imaging with the capsule endoscope.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
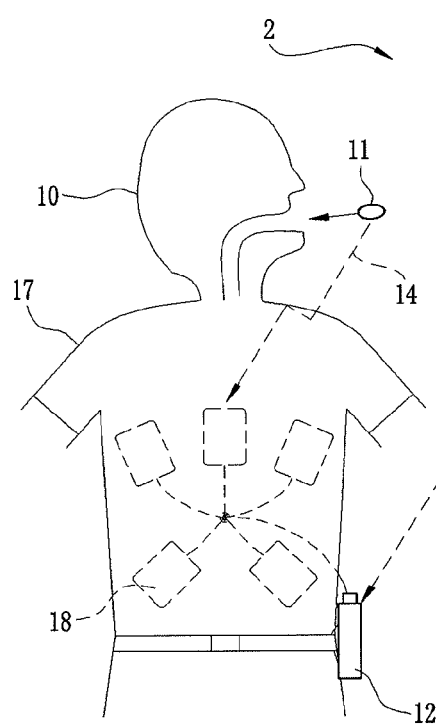
FIG. 1A is an explanatory view in elevation illustrating a human body, a capsule endoscope and a receiver in a capsule endoscope system.
Figure 1B:
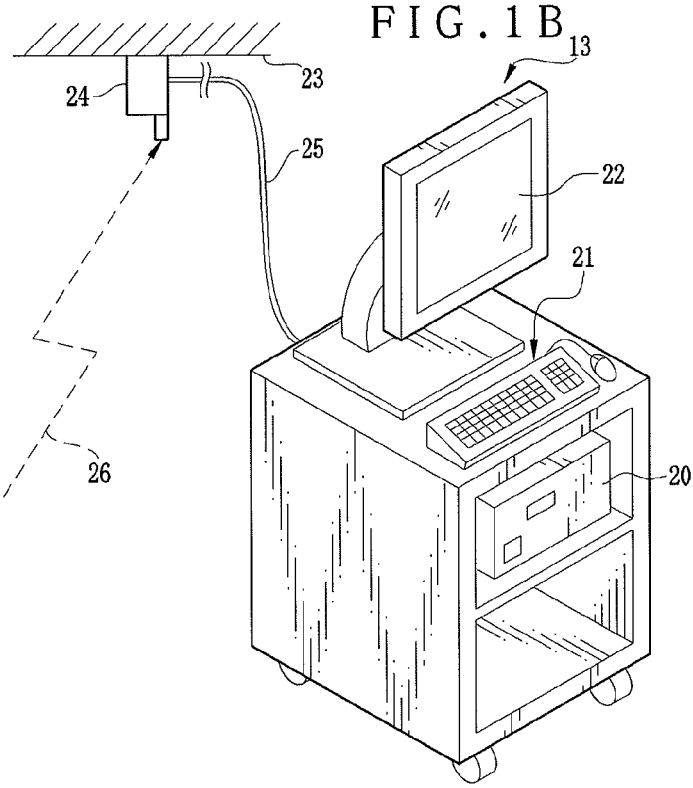
FIG. 1B is a perspective view illustrating a workstation in the capsule endoscope system.

In FIGS. 1A and 1B, a capsule endoscope system 2 includes a capsule endoscope 11, a receiver 12, and a workstation 13 for image filing. The capsule endoscope 11 is orally swallowed in a human body 10 of a patient. The receiver 12 is attached on a belt with which the receiver 12 is positioned on the human body 10. The workstation 13 retrieves images from the capsule endoscope 11 for a doctor or physician to read the images.

The capsule endoscope 11 picks up an image of an inner surface of the gastrointestinal tract in the human body 10 at a predetermine frame rate, for example 2 fps (frames per second). A radio wave 14 of image data is emitted and transmitted by the capsule endoscope 11 to the receiver 12. Details of the capsule endoscope 11 are known and are not described further herein, including a structure of the capsule endoscope 11, image pickup and wireless transmission of the capsule endoscope 11 and the like.

The receiver 12 receives image data from the capsule endoscope 11 wirelessly with the radio wave 14, and stores the image data. A shielding shirt 17 is worn by the human body 10 of the patient. Plural antennas 18 are attached inside the shielding shirt 17. For communication between the capsule endoscope 11 and the receiver 12 with the radio wave 14, an antenna (not shown) in the capsule endoscope 11 and the antennas 18 are used. The receiver 12 wirelessly transmits image data to the workstation 13 by use of radio wave.

The workstation 13 as information manager of the invention includes a processor 20, an input interface 21, and an LCD display panel 22. The input interface 21 includes a keyboard, mouse or the like. In an examination room, the processor 20 is installed. A ceiling 23 of the examination room is provided with an antenna 24. An antenna cable 25 connects the antenna 24 with the processor 20. A radio wave 26 is received from the receiver 12 by the antenna 24 for communication of various data. During examination with the capsule endoscope 11, the processor 20 receives image data wirelessly transmitted from the receiver 12 with the radio wave 26, and files image data per one patient. Also, a display image is created from image data and displayed on the LCD display panel 22.

The receiver 12 can wirelessly transmit image data from the capsule endoscope 11 to the processor 20, namely the workstation 13, in an instantaneous manner. If all of the image data from the capsule endoscope 11 are treated for transmission by the receiver 12 to the processor 20, it is likely that plural image data of images for a common body part are included in the treated image data. This occurs typically when the capsule endoscope 11 remains within the human body 10, as a plurality of images are recorded for nearly the same body part. Load to a doctor will increase, because numerous images with small significance must be observed and cause low efficiency. Data storage 48 of FIG. 2 for storing image data must have a large capacity, and will raise the cost.

The receiver 12 wirelessly transmits selected image data to the processor 20, namely image data of necessary frame images other than unnecessary frame images useless in the diagnosis, the selected image data being selected by removing part of image data of a substantially common body part. For selecting the image data of necessary frame images, the processor 20 operates for the selection so that the receiver 12 can be constructed in a simplified manner.

Figure 2:
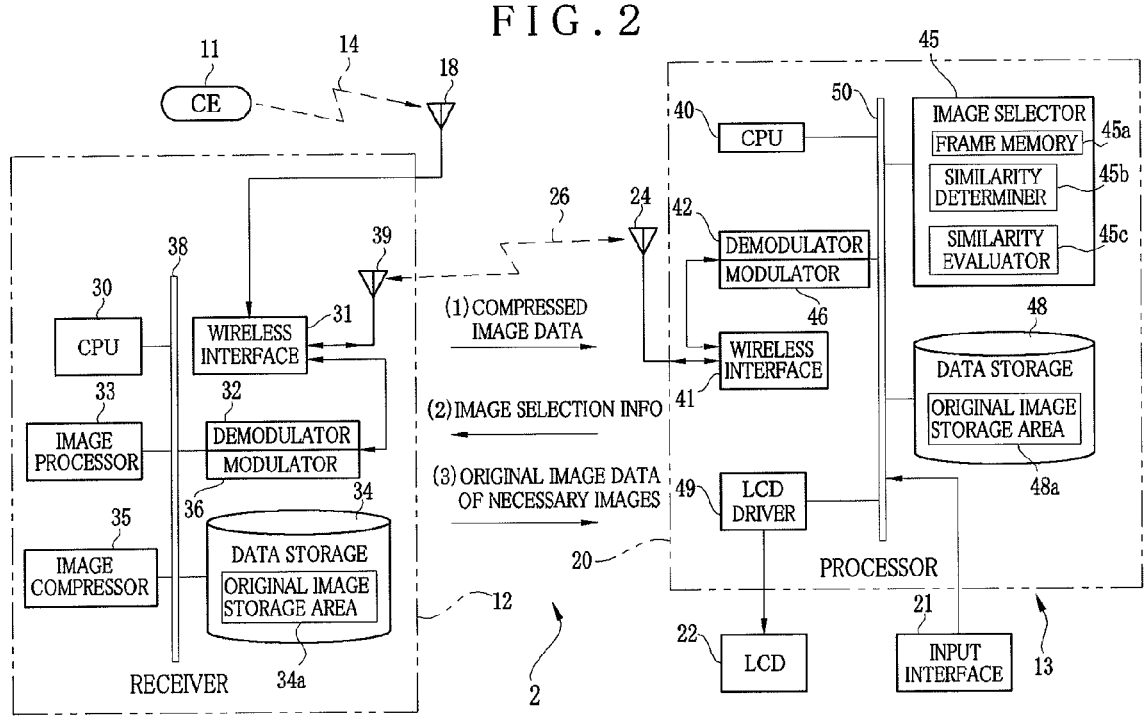
FIG. 2 is a block diagram illustrating circuit elements in the capsule endoscope system.

In FIG. 2, the receiver 12 reduces a data size of image data received wirelessly from the capsule endoscope 11 and transmits the image data to the processor 20. Then the processor 20 selects necessary frame images from images of the wirelessly received image data, so that image data of the necessary frame images are transmitted to the receiver 12. After this, the receiver 12 in response to the selection of the necessary frame images transmits only original image data of the necessary frame images to the processor 20 wirelessly.

The receiver 12 includes a CPU 30, a wireless communication interface 31, a demodulator 32, an image processor 33, data storage 34, an image compressor 35 as data size reduction device to reduce a data size, and a modulator 36. There is a data bus 38 with which those elements except for the wireless interface 31 are interconnected. An antenna 39 is connected with the wireless interface 31. The CPU 30 controls various elements of the receiver 12 as entirety.

The wireless interface 31 in connection with the antennas 18 amplifies and filters the radio wave 14 by bandpass filtering, and then inputs the signal of the radio wave 14 to the demodulator 32. The demodulator 32 converts the radio wave 14 from the wireless interface 31 to original image data by demodulation. The image processor 33 is supplied with the original image data.

The image processor 33 processes original image data from the demodulator 32 in various types of image processing. The processed original image data is assigned with ID information by the CPU 30, such as a file name, and is stored in a RAM or the like in a temporary manner. The CPU 30 sends the original image data from the RAM to the data storage 34 and the image compressor 35. An original image storage area 34a in the data storage 34 stores the original image data of images.

The image compressor 35 compresses image data to reduce a data size of original image data. An example of the compression is the compression encoding. The compression encoding is a process of converting image data to other data with a smaller data size but with substantially the same property. Examples of the compression encoding include lossless compression (e.g. GIF) in which data can be decompressed again to an original form before the compression, and lossy compression (e.g. JPEG) in which data cannot be decompressed to an original form before the compression. The image compressor 35 compresses the original image data, which is written to a transmission image memory (not shown). When compressed image data of images of a predetermined image number are stored in the transmission image memory, the CPU 30 outputs those to the modulator 36.

The modulator 36 modulates compressed image data from the transmission image memory into a signal of the radio wave 26, which is output to the wireless interface 31. The wireless interface 31 amplifies and filters the signal of the radio wave 26 in the bandpass filtering, and causes the antenna 39 to emit the radio wave 26. Thus, the compressed image data is wirelessly transmitted from the receiver 12 to the processor 20 in the workstation 13.

The processor 20 includes a CPU 40, a wireless communication interface 41, a demodulator 42, an image selector 45, a modulator 46, the data storage 48 and an LCD driver 49. There is a data bus 50 which interconnects those except for the wireless interface 41. The CPU 40 controls the entirety of the processor 20.

The antenna 24 is connected to the wireless interface 41. The wireless interface 41 operates to communicate together with the CPU 40. When the radio wave 26 is received by the antenna 24, the wireless interface 41 amplifies and filters the radio wave 26 in bandpass filtering. A signal of the radio wave 26 is input to the demodulator 42. The demodulator 42 demodulates the signal of the radio wave 26 to provide original compressed image data, which is successively written to a reception image memory (not shown). When the compressed image data of a predetermined image number are written to the reception image memory, images of those image data are output to the image selector 45 by one image.

The image selector 45 selects compressed image data of necessary images which are included in compressed image data of images of a predetermined image number but are different from unnecessary images obtained from nearly the same body part. For the purpose of this selection, similarity degree between preceding and succeeding images (or difference degree) is determined and evaluated according to similarity between compressed image data of consecutively recorded images.

The image selector 45 includes a frame memory 45a, a similarity determiner 45b and a similarity evaluator 45c. The frame memory 45a stores compressed two image data of preceding and succeeding frame images from the demodulator 42, and is accessed to overwrite compressed image data of the preceding image with new compressed image data by rewriting successively at each time of checking similarity between the preceding and succeeding frame images. For example, let N be an integer equal to or more than 2. When similarity between compressed image data of the (N−1)th image and the Nth image is found to be high, compressed image data of the (N−1)th image (preceding image) is overwritten with compressed image data of the (N+1)th image by rewriting.

The similarity determiner 45b determines similarity degree between preceding and succeeding frame images read from the frame memory 45a. An equation for determining similarity in the similarity determiner 45b is a function in which a result value is higher according to highness in the similarity between the two feature values. The following is an example of the equation of the similarity degree D1.

$$D1 = c1 - \Sigma(g1_i - g2_i)^2$$

where g1 is a pixel value of a frame image 1,
g2 is a pixel value of a frame image 2,
i is a pixel number,
c1 is a constant.

Specifically, a luminance signal (Y signal) is derived from compressed image data of preceding and succeeding frame images, to obtain pixel values (luminance values) of all pixels in a sampling area constituted by n×m pixels (n and m are integers) in those frame images. Then for all the pixels in the sampling area of those frame images, a difference of pixel values of the pixels is obtained. A square of the difference is obtained, and added up to determine a difference square sum of the pixel values. The sum is subtracted from a constant, so that a difference is obtained to be the similarity degree. Information of the similarity degree is input to the similarity evaluator 45c.

The similarity evaluator 45c evaluates information of the similarity obtained by the similarity determiner 45b, and checks whether a succeeding image read from the frame memory 45a is similar to a preceding image, or whether the succeeding image is necessary or unnecessary. If the similarity degree is equal to or more than the threshold value, the succeeding image is found to be unnecessary because of high similarity between the two. If the similarity degree is less than the threshold value, the succeeding image is found to be necessary because of a difference between the two. Note that the similarity evaluator 45c determines that a first image according to compressed image data among images in the entire image sequence is a necessary frame image.

Figure 3:
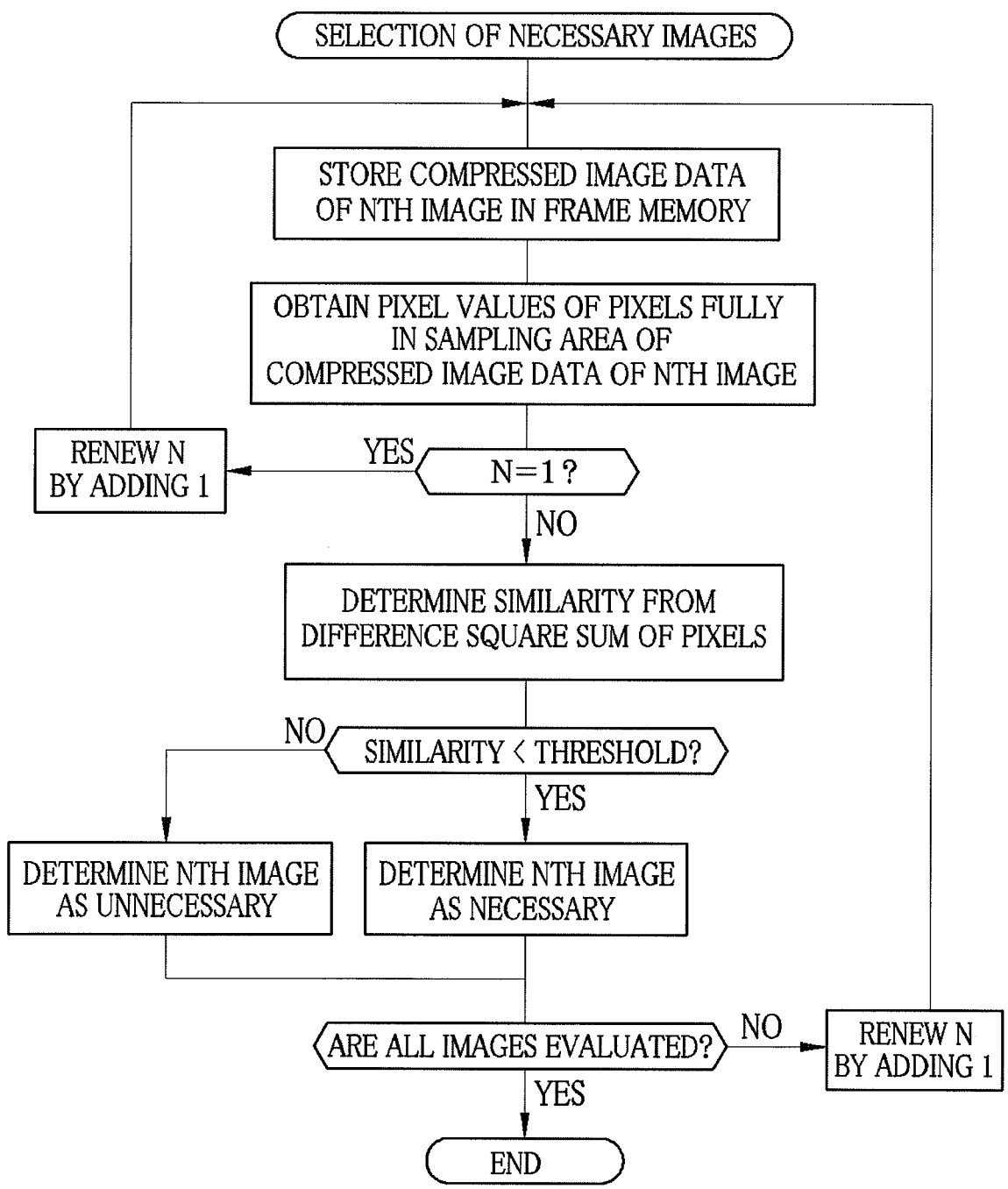
FIG. 3 is a flow chart illustrating a selecting operation in an image selector.

Selecting operation for necessary frame images in the image selector 45 is described now. In FIG. 3, the image selector 45 writes compressed image data of a first image to the frame memory 45a among compressed image data of a predetermined image number input by the demodulator 42. The similarity determiner 45b determines pixel values of all the pixels in the sampling area of the compressed image data of the first image stored in the frame memory 45a. Also, the similarity determiner 45b determines the first image as a necessary frame image.

Then the image selector 45 writes compressed image data of a second image to the frame memory 45a. The similarity determiner 45b determines pixel values of all the pixels in the sampling area of the compressed image data of the second image. Then the similarity determiner 45b determines similarity degree between pixel values of compressed image data of a first image (preceding image) and pixel values of compressed image data of a second image (succeeding image). Then information of the similarity degree is input to the similarity evaluator 45c.

If the similarity degree from the similarity determiner 45b is less than a threshold value, then the similarity evaluator 45c determines a second image of compressed image data as a necessary image. If the similarity degree from the similarity determiner 45b is equal to or more than the threshold value, then the similarity evaluator 45c determines the second image of compressed image data as a unnecessary image.

When the second image of the compressed image data is found to be a necessary or unnecessary frame image, then the image selector 45 overwrites compressed image data of a first image from the frame memory 45a with compressed image data of a third image by rewriting. The similarity determiner 45b determines pixel values of all pixels in a sampling area of compressed image data of a first image, and also determines the similarity degree by use of the pixel values and those of compressed image data of a second image obtained previously. According to the determined similarity degree, the similarity evaluator 45c checks whether an image of the third compressed image data is a necessary or unnecessary frame image.

Similarly, the similarity determiner 45b determines similarity degree by use of the pixel values of compressed image data of (N−1)th and Nth images. The similarity evaluator 45c checks whether the Nth image of the compressed image data is a necessary frame image or not. The information of the evaluation result is written to a memory (not shown) in the image selector 45 successively in association with respective image data. When the evaluation is completed for all of the compressed image data input by the demodulator 42 (or when N comes up to be a predetermined image number), then the selecting operation of the image selector 45 is completed. The selecting operation is repeated at each time of inputting compressed image data of images of a predetermined image number from the receiver 12 to the processor 20 in the workstation 13.

Note that, if the second image of the compressed image data is determined as unnecessary frame image, it is possible to check whether compressed image data of a third image is similar with compressed image data of a first image being a necessary frame image with highest closeness of time, in place of compressed image data of the second image as unnecessary frame image. In short, it is possible to keep the preceding image without rewriting until a succeeding image is determined as necessary frame image.

Again, with reference to FIG. 2, the image selector 45 after the determination extracts ID information of compressed image data of which an image is found to be a necessary frame image among compressed image data of images of a predetermined image number stored in a memory, and forms image selection information according to the ID information. Then the CPU 40 outputs the image selection information from the image selector 45 to the modulator 46.

The modulator 46 modulates image selection information from the image selector 45 into a signal of the radio wave 26, which is output to the wireless interface 41. The wireless interface 41 responsively causes the antenna 24 to emit the radio wave 26. Thus, the image selection information is wirelessly transmitted by the processor 20 in the workstation 13 to the receiver 12.

The radio wave 26 emitted by the antenna 24 is received by the antenna 39 of the receiver 12, and processed by the wireless interface 31 and the demodulator 32 of demodulation to create the image selection information of an original form. The CPU 30 searches and retrieves original image data of necessary frame images from the original image storage area 34a in correspondence with ID information included in the image selection information after demodulation. Original image data are successively stored in the transmission image memory. After the retrieval, the CPU 30 outputs original image data of necessary frame images from the transmission image memory to the modulator 36.

The modulator 36 modulates original image data of a necessary frame image into a signal of the radio wave 26, which is output to the wireless interface 31. In response, the wireless interface 31 causes the antenna 39 to emit the radio wave 26. Thus, original image data of the necessary frame image is wirelessly transmitted from the receiver 12 to the processor 20.

Note that original image data of images other than necessary frame images are abandoned from the original image storage area 34a, or compressed and stored. The abandonment of original image data of unnecessary frame images can reduce a total amount of image data for storing in the original image storage area 34a or the data storage 34. Thus, the cost will be reduced because the data storage 34 for use can have a smaller capacity. Also, storing compressed image data after compressing original image data of unnecessary frame images enables compensation, at the time of an error in selecting compressed image data.

The radio wave 26 emitted by the antenna 39 is received by the antenna 24, and is input to the processor 20. The radio wave 26 in the processor 20 is demodulated by the demodulator 42 to provide original image data, which is successively stored in a reception image memory. Upon completion of the demodulation, the CPU 40 outputs all of the original image data from the reception image memory to the data storage 48, and written to an original image storage area 48a. When a doctor operates the input interface 21, original image data is read from the original image storage area 48a, and converted into a display image, which is displayed on the LCD display panel 22.

Figure 4:
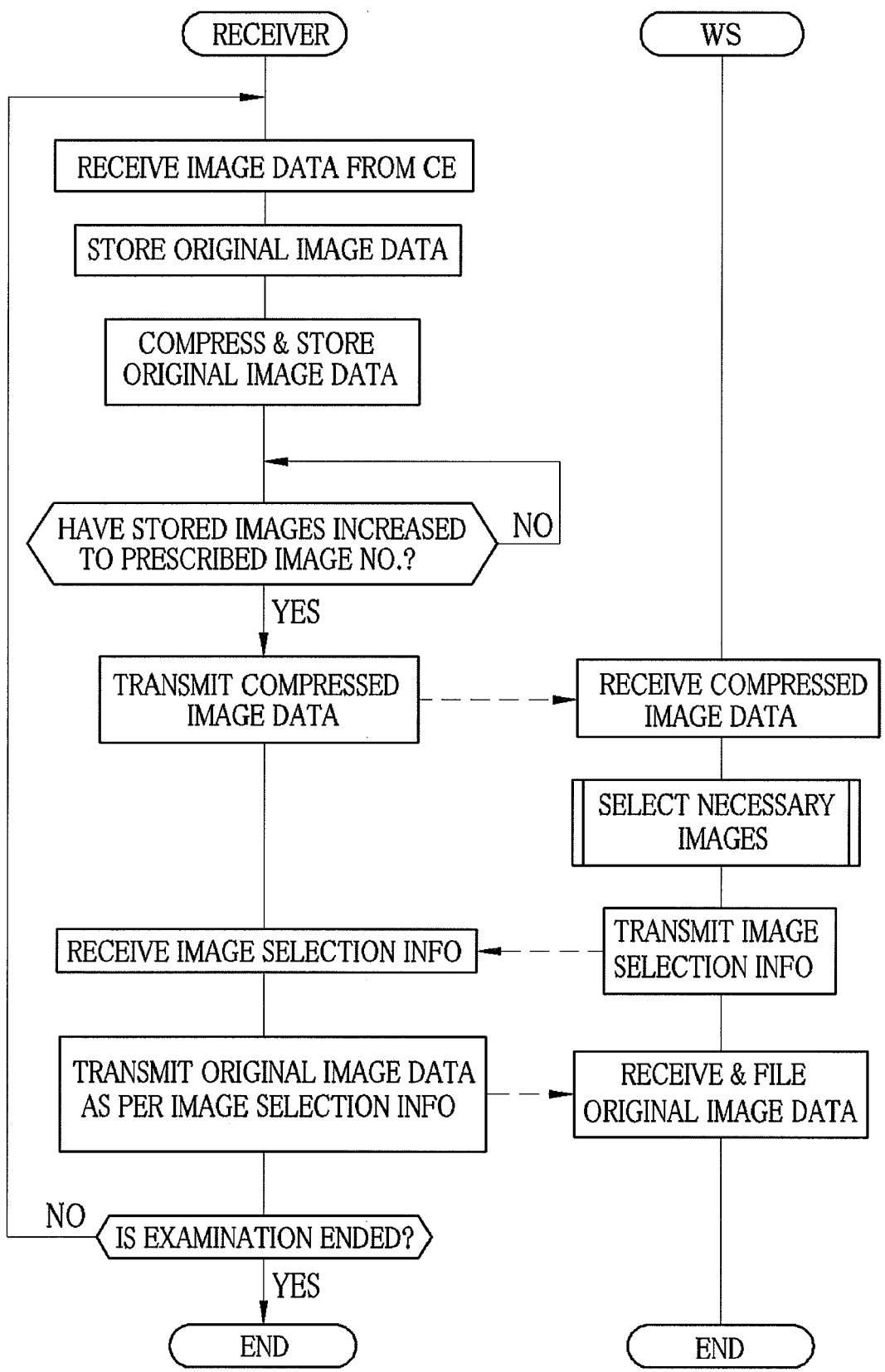
FIG. 4 is a flowchart illustrating transmission of original image data from a receiver to a workstation.

Operation of the capsule endoscope system 2 in the examination is described now by referring to FIG. 4. At first, a doctor instructs the patient to wear the shielding shirt 17 together with the receiver 12 and the antennas 18. A power source in the capsule endoscope 11 is turned on. The patient is caused to swallow the capsule endoscope 11 orally. The capsule endoscope 11 picks up an image of an inner surface of the gastrointestinal tract at a frame rate of 2 fps. Image data is created, and successively transmitted wirelessly with the radio wave 14.

The radio wave 14 output by the capsule endoscope 11 is received by the antennas 18 of the shielding shirt 17, and input to the wireless interface 31 of the receiver 12. The radio wave 14 in the wireless interface 31 is demodulated by the demodulator 32 to provide original image data, which is processed by the image processor 33 for image processing of various items. The original image data after the image processing is assigned by the CPU 30 with ID information, and is stored in the RAM or the like. The CPU 30 reads the original image data from the RAM and outputs the same to the data storage 34 and the image compressor 35.

In the data storage 34, the original image data are stored in the original image storage area 34a. The image compressor 35 as data size reduction device compresses the original image data frame after frame. The original compressed image data from the image compressor 35 are written by the CPU 30 to a transmission image memory (not shown) successively. Then the CPU 30 outputs stored compressed image data to the modulator 36 when images of the stored compressed image data in the transmission image memory increase to a predetermined image number. The compressed image data of the images of the predetermined image number are modulated by the modulator 36 into the radio wave 26, which is processed in the wireless interface 31 and emitted by the antenna 39.

The radio wave 26 from the antenna 39 is received by the antenna 24, demodulated by the processor 20 to provide original compressed image data, which is stored to a receiving image memory. When compressed image data of a predetermined image number is stored in the receiving image memory, the CPU 40 sends the compressed image data to the image selector 45. The image selector 45 selects necessary frame images among images of the compressed image data of the predetermined image number, as has been described with FIG. 3.

When the selecting operation with the image selector 45 is terminated, the CPU 40 outputs the image selection information from the image selector 45 to the modulator 46. The image selection information is modulated into the radio wave 26, which is emitted by the antenna 24.

The radio wave 26 emitted by the antenna 24 is received by the antenna 39 of the receiver 12, and demodulated to provide image selection information of an original form. The CPU 30 searches original image data from the original image storage area 34a according to the ID information in the image selection information. As has been described above, the CPU 30 modulates the original image data of the necessary frame image into the radio wave 26, which is emitted by the antenna 39. The CPU 30 deletes or compresses original image data of images other than the necessary frame image in the original image storage area 34a, the compressed original image data being written to the data storage 34.

The radio wave 26 emitted by the antenna 39 is received by the antenna 24, and demodulated by the processor 20 to provide original image data of a necessary frame image, which is written to the original image storage area 48a of the data storage 48. Before the completion of endoscopic examination, this sequence is repeated at each time of receiving image data in the receiver 12 from the capsule endoscope 11.

When the capsule endoscope 11 picks up images, a doctor operates the input interface 21 to select images of image data of interest for image reading among original image data stored in the original image storage area 48a. The selected original image data are read by the CPU 40 from the original image storage area 48a and converted into display images, which are displayed on the LCD display panel 22. He or she reads images on the LCD display panel 22 for diagnosis.

In conclusion, image data of endoscopic images in the capsule endoscope system 2 can be wirelessly transmitted from the receiver 12 to the processor 20 in the workstation 13 while the images are created in the capsule endoscope 11. It is possible to start the image reading without waiting for the finish of the imaging for the examination. Thus, a result of the diagnosis can be obtained rapidly, because the image reading of all the images can be finished no later than the discharge of the capsule endoscope 11 from the human body 10. Treatment for the human body 10 in a hospital can be carried out quickly according to the result of the diagnosis.

It is possible in the invention for the receiver 12 wirelessly to transmit original image data of necessary frame images to the workstation 13. Unnecessary frame images for a common body part can be eliminated, so that a doctor can read only necessary frame images. Thus, load to the doctor for image reading can be reduced. Also, the data storage 48 for the processor 20 can have a smaller capacity than that used conventionally, so that the cost can be reduced. Time for the doctor to diagnose images can be decreased because the amount of images to be stored in the data storage 48 can be reduced.

It is also possible to simplify the structure of the receiver 12 because necessary frame images are selected in the processor 20 of the workstation 13. Although wireless transmission of image data from the capsule endoscope 11 directly to the workstation 13 is conceivable, there are shortcomings in that the wireless interface 31 of the capsule endoscope 11 may have a considerably large size, or that a battery may be very large in compliance with high power, for the purpose of the ensured high power for the wireless transmission. However, it is possible in the invention to construct the receiver 12 and the workstation 13 with small modifications without modifying the capsule endoscope 11.

In the embodiment of FIG. 4, it is possible that the reception of image data from the capsule endoscope 11 is simultaneous with selection of a necessary frame image and transmission. Also, original image data from the receiver 12 to the workstation 13 may be processed in the compression encoding. The compression can be any one of the lossy compression and the lossless compression in which parameters are determined to maintain higher image quality than compressed image data.

Another preferred embodiment of the invention is described now. In the first embodiment, the difference square sum of the pixel values of the images is utilized to evaluate similarity between the images. In contrast, in the present embodiment, similarity between preceding and succeeding frame images is evaluated according to detection of a motion vector from the preceding frame image to the succeeding frame image. To this end, the similarity determiner 45b in the image selector 45 determines the motion vector, according to which the similarity evaluator 45c evaluates similarity between the frame images. See FIG. 2.

The similarity determiner 45b determines a motion vector according to a feature point matching method. According to this, one pixel included in those in a sampling area of a preceding image is determined as a representative pixel before motion. A pixel value of the representative pixel before motion is detected. Also, pixel values of pixels in a sampling area of a succeeding image are detected. One of pixels is designated, at which an absolute value of a difference (or difference square sum of the pixel values) between the pixel value of the representative pixel before the motion and the detected pixel values of pixels in the sampling area in the succeeding image becomes the smallest. Thus, a motion vector is determined by way of a vector of which a starting point is a representative pixel before motion and an endpoint is a representative pixel after motion. Information of the motion vector is input to the similarity evaluator 45c. Note that it is possible to use methods other than the feature point matching method to determine a motion vector, for example, matching for a unit of a block of k1×k2 pixels (k1 and k2 are integers equal to or more than 1). In the present embodiment, the similarity degree between the images is small according to greatness in the size of the motion vector.

If a shift amount of the motion vector input by the similarity determiner 45b is found equal to or less than a threshold value, then the similarity evaluator 45c determines that there is high similarity between the preceding and succeeding images, and that the succeeding image is an unnecessary frame image. If the shift amount of the motion vector is found more than the threshold value, then the similarity evaluator 45c determines that there is a difference between the preceding and succeeding images, and that the succeeding image is a necessary frame image.

Figure 5:
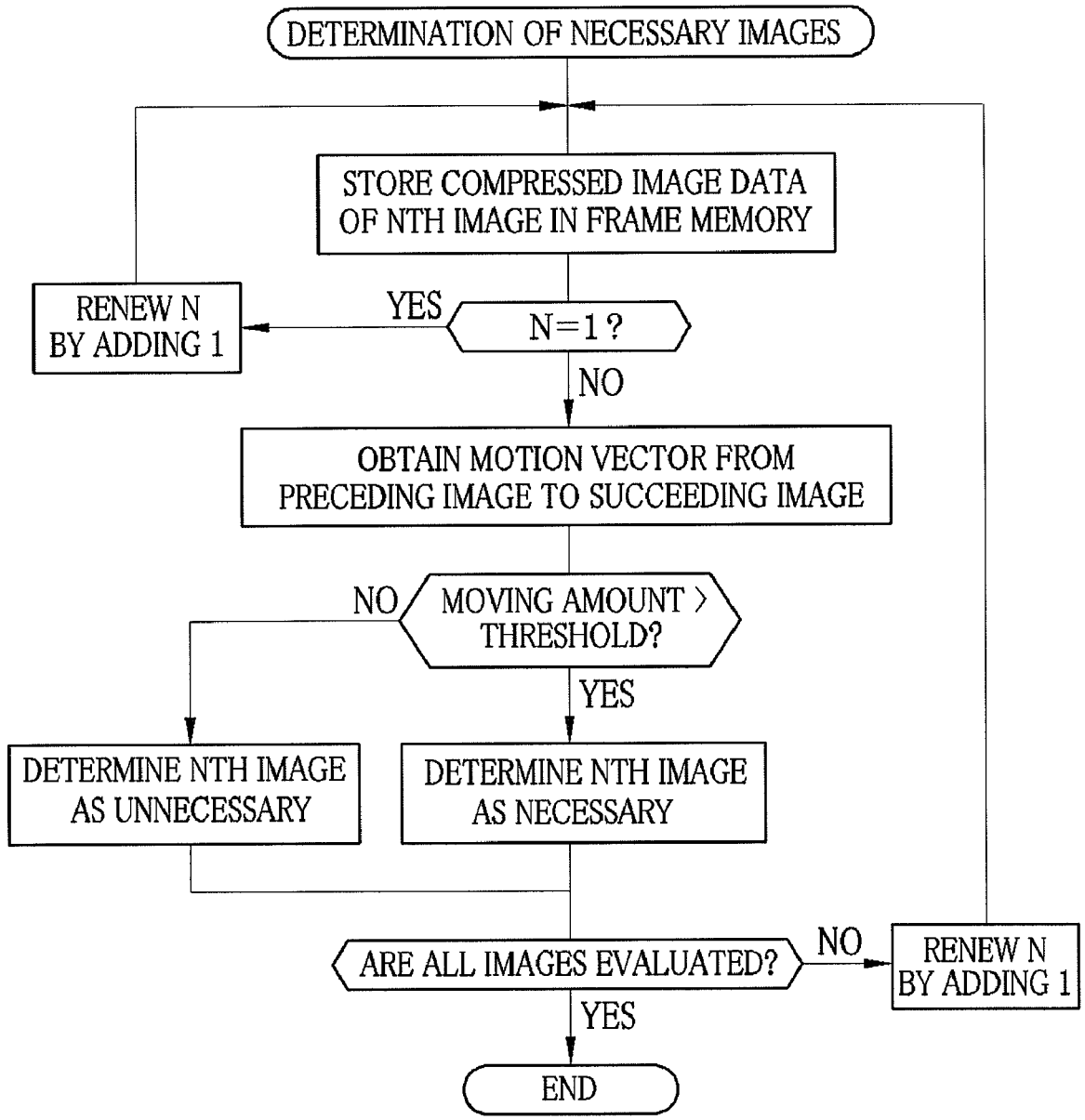
FIG. 5 is a flow chart illustrating a selecting operation in an image selector in a second preferred embodiment.

With reference to FIG. 5, selection of necessary frame images in the embodiment is described. When compressed image data of the first and second images are stored in the frame memory 45a, the similarity determiner 45b determines a motion vector of the compressed image data of the second image with reference to the compressed image data of the first image by use of the above-described method of the motion vector estimation. The obtained motion vector is input to the similarity evaluator 45c.

If a shift amount of the motion vector input by the similarity determiner 45b is found more than a threshold value, then the similarity evaluator 45c determines that the second image of compressed image data is a necessary frame image. If the shift amount of the motion vector is found equal to or less than the threshold value, then the similarity evaluator 45c determines that the second image of compressed image data is an unnecessary frame image.

When the evaluation is completed, the image selector 45 overwrites compressed image data of a first image in the frame memory 45a with compressed image data of a third image by rewriting. Also, the similarity determiner 45b determines a motion vector from the (N−1)th image of compressed image data (preceding image) to the Nth image (succeeding image). The similarity evaluator 45c checks whether the Nth image of compressed image data is a necessary or unnecessary frame image. This is followed by a process which is the same as that of the first embodiment.

Similarity can be evaluated in the invention by methods other than those of the first and second embodiments in which the difference square sum or motion vector is utilized. For example, the similarity determiner 45b can detect distribution of density, distribution of the color balance or the like of the preceding and succeeding frame images according to the known techniques of the image recognition. Similarity degree between those is determined according to the detected distribution or the like to evaluate the similarity between the preceding and succeeding frame images. For the selecting operation in the present embodiment, the process according to the first embodiment of FIG. 3 is repeated.

Another preferred embodiment is described now. Although the image selector 45 in the above embodiments selects necessary frame images by evaluating similarity of preceding and succeeding images, selection may be carried out differently. For example, it is possible as necessary frame images to select images with similarity to sample images previously obtained from typical cases, among images of compressed image data of a predetermined image number received from the receiver 12. Selection of necessary frame images will be hereinafter described specifically.

Examples of sample image data include collected image data of lesions in body parts of other patients after endoscopic examination with a capsule endoscope, image data of typical lesions with characteristics of a typical shape, color, size and the like, and image data of foreign material such as parasites, food particles and the like.

Figure 6:
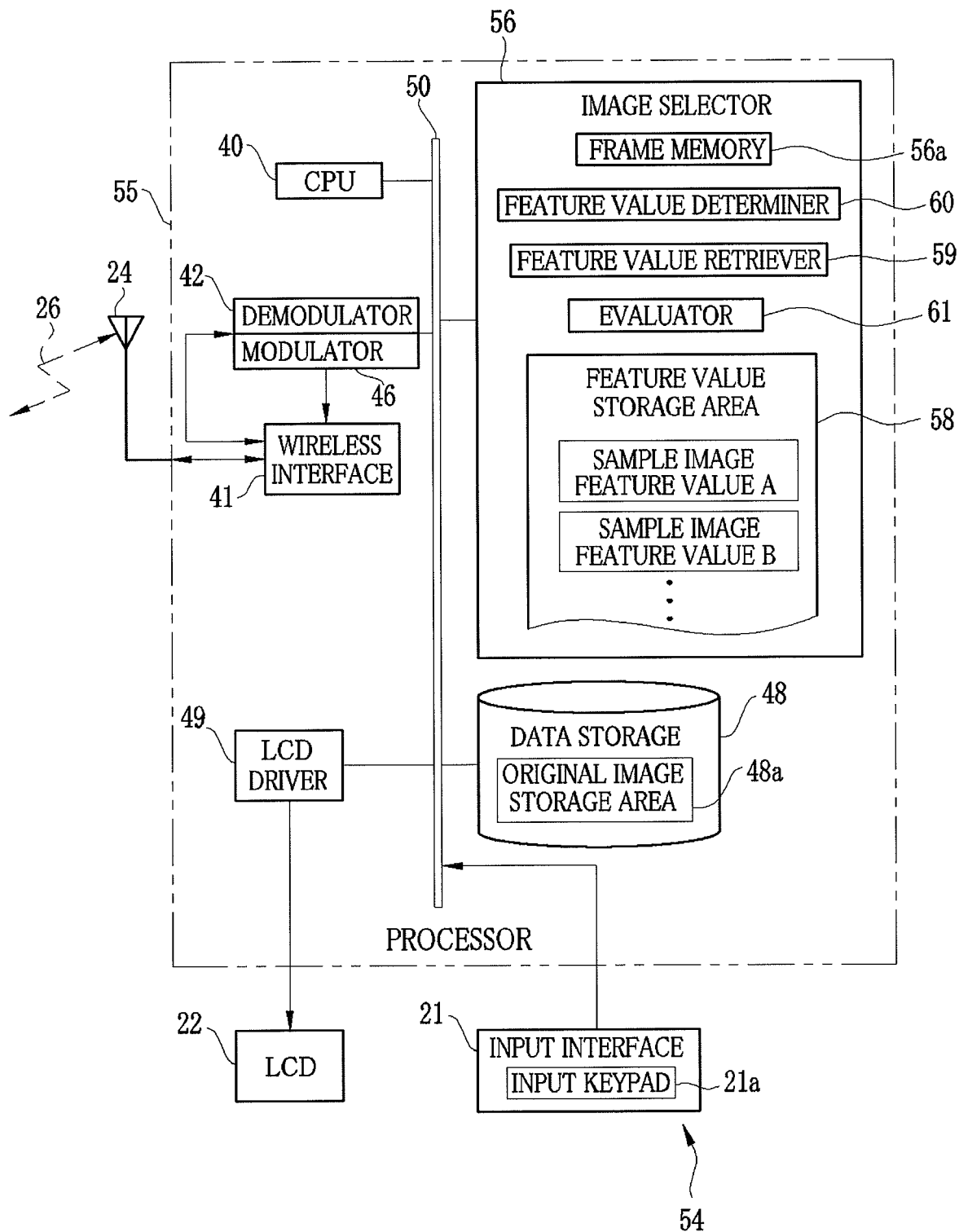
FIG. 6 is a block diagram illustrating circuit elements in a workstation in a third preferred embodiment.

In FIG. 6, a processor 55 in a workstation 54 for image filing in still another embodiment is constructed by repeating the processor 20 but with a difference of having an image selector 56 in place of the image selector 45. Elements similar to those of the above embodiments are designated with identical reference numerals.

The image selector 56 responds to compressed image data of images of a predetermined image number received from the receiver 12, and selects compressed image data with similarity to sample image data as necessary frame images. The image selector 56 includes a frame memory 56a, a feature value storage area 58, a feature value retriever 59, a feature value determiner 60 and an evaluator 61. The frame memory 56a stores one frame of compressed image data, and is accessed to overwrite evaluated compressed image data with new compressed image data by rewriting at each time of evaluating similarity with sample image data.

The feature value storage area 58 stores image feature values (values A, B and so on) of a plurality of sample image data which are different between types of lesions. Examples of the image feature values are feature values of color balance of images in the entirety, color distribution, distribution of contour lines, image data of forms and the like, and expressed numerically. The image feature values A, B and so on are stored in the feature value storage area 58 in a sorted manner for the types of lesions. Note that type information may be determined for types of the lesions and assigned with data of the image feature values A, B and so on.

The image feature values A, B and so on are read at the time of selecting operation of necessary frame images in the image selector 56. There arises a problem of excessively long time in processing, because of checking whether compressed image data has similarity degree in comparison with sample image data by reading the image feature values A, B and so on at one time.

It is possible to read only a sample image feature value according to a lesion type (purpose of examination) in endoscopic examination for the purpose of diagnosing predetermined lesions, such as polyp, erosion, tumor and the like. To this end, an input keypad 21a for examination information in the input interface 21 is disposed and adapted to inputting examination information including information of a lesion type.

When the examination information is input with the input keypad 21a, the feature value retriever 59 searches and reads a sample image feature value from the feature value storage area 58 according to the examination information, and inputs the sample image feature value to the evaluator 61.

The feature value determiner 60 extracts an image feature value from compressed image data stored in the frame memory 45a. A method of extracting the image feature value from image data may be a known method, and is not described further herein. Information of the image feature value is input to the evaluator 61.

The evaluator 61 compares the image feature value from the feature value determiner 60 with the sample image feature value from the feature value retriever 59. An equation for determining similarity in the evaluator 61 is a function in which a result value is higher according to highness in the similarity between the two feature values. The following is an example of the equation of the similarity degree D2.

$$D2 = c2 - \Sigma[a_i \cdot (vx_i - vs_i)^2]$$

where vx is the image feature value of the endoscopic image,
vs is the sample image feature value,
$a_i$ is a weighting coefficient for each of parameters,
i is a parameter number,
c2 is a constant.

Note that the image feature value may be a plurality of parameters. According to this, the number of the parameter numbers i is 2 or more.

Also, it is possible in the evaluator 61 to determine that the compressed image data from the frame memory 45a is similar to the sample image data and is image data of a necessary frame image if the similarity degree between the image feature values is equal to or more than the predetermined threshold value. Also, one or more images before or after a necessary frame image of the compressed image data are determined as necessary frame images. If the similarity degree between the image feature values is less than the threshold value, the images are determined as unnecessary frame images, because the compressed image data from the frame memory 45a are not similar to the sample image data.

Figure 7:
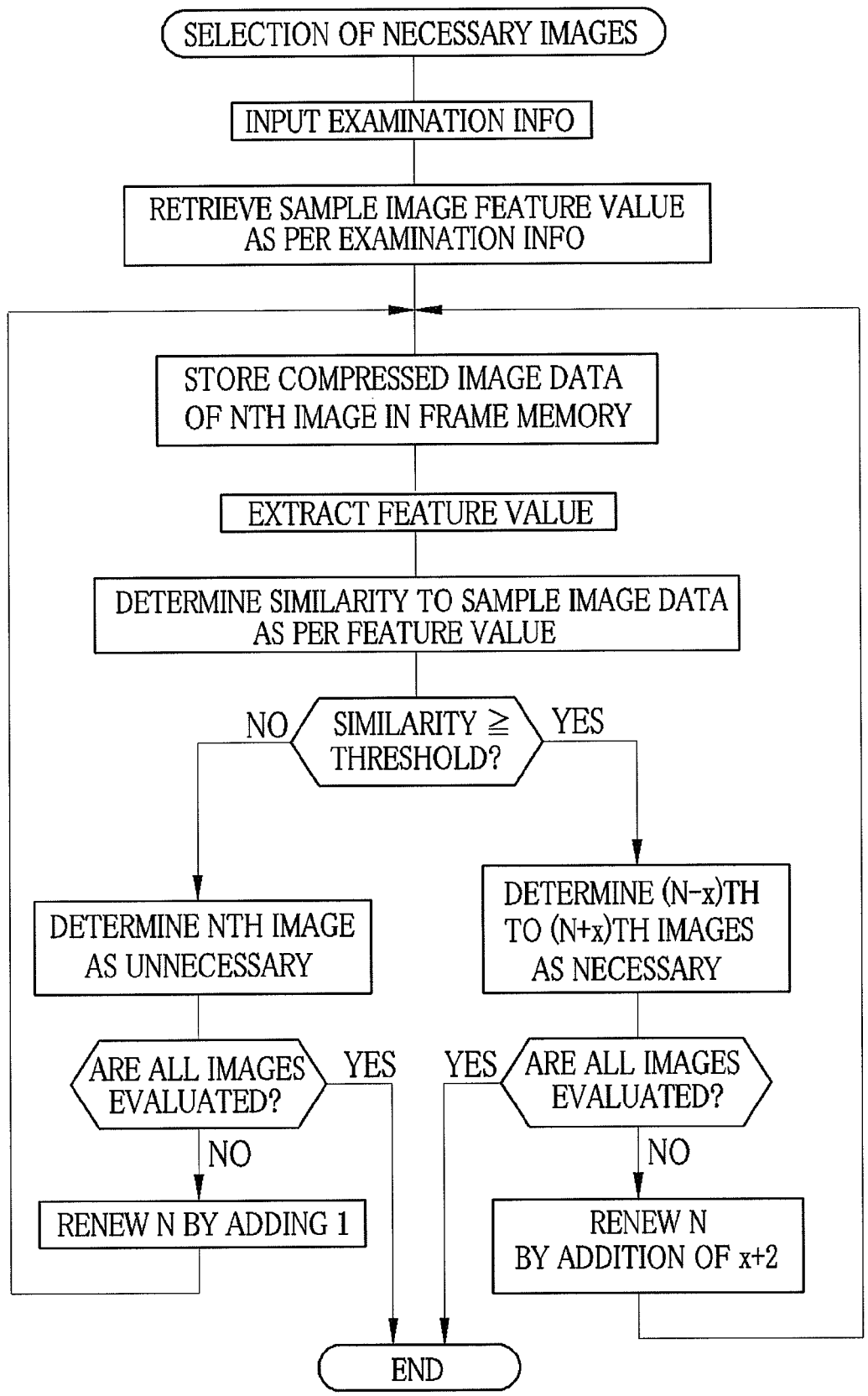
FIG. 7 is a flow chart illustrating a selecting operation in an image selector in the embodiment of FIG. 6.

Selection of necessary images in the image selector 56 is described now by referring to FIG. 7. At first, a doctor or physician inputs examination information with the input keypad 21a of the input interface 21. The feature value retriever 59 searches and reads a sample image feature value from the feature value storage area 58 in correspondence with the input examination information, to input the sample image feature value to the evaluator 61.

Upon a start of endoscopic imaging, the image selector 56 of the processor 55 selects compressed image data of a first image among compressed image data received from the receiver 12, and writes the selected compressed image data to the frame memory 56a. The feature value determiner 60 extracts an image feature value from the compressed image data of the first image in the frame memory 56a, and outputs the image feature value to the evaluator 61.

The evaluator 61 determines similarity degree by comparison with the image feature value of the compressed image data of the first image and the sample image feature value retrieved according to the examination information. If the similarity degree is equal to or more than the threshold value, then the evaluator 61 determines that the first image and x images (x is an integer) of image data as necessary frame images. When the evaluator 61 determines that the images of the compressed image data of the first image to the (x+1)th image as necessary frame images, then the image selector 56 overwrites compressed image data of the first image with compressed image data of an (x+2)th image in the frame memory 56a by rewriting.

In contrast, the evaluator 61 determines the first image of image data as unnecessary frame image if the similarity degree is equal to or less than the predetermined threshold value. In response to this result, the image selector 56 overwrites compressed image data of the first image with compressed image data of a second image by rewriting in the frame memory 56a.

Similarly, the feature value determiner 60 derives an image feature value of compressed image data of an Nth image, and inputs the same to the evaluator 61. The evaluator 61 checks whether the Nth image of the compressed image data is a necessary frame image. If it is found to be a necessary frame image, then the (N−x) th image to the (N+x) th image are found to be a necessary frame images (wherein N−x≧1). This is followed by steps in the process of the first embodiment.

In the embodiment, only compressed image data of images with similarity to sample images of sample image data according to a purpose of examination (type of lesion of interest for image reading). It is possible wirelessly to transmit original image data of images to the processor 55 with only lesions of which a doctor needs to read images. Thus, load of the doctor for image reading can be decreased.

In the present embodiment, if no examination information is input with the input keypad 21a, all of the sample image feature values stored in the feature value storage area 58 can be input by the feature value retriever 59 to the evaluator 61. According to determined similarity degree between the compressed image feature value and sample image feature values, an image of the sample image data is determined as a necessary frame image if there is high similarity of the compressed image feature value to any one of the sample image feature values.

It is possible with the input keypad 21a to input information of plural lesion types as examination information. In response to this, the feature value retriever 59 searches and reads a plurality of sample image feature values from the feature value storage area 58, and inputs those to the evaluator 61.

In the first, second and third embodiments, the receiver 12 transmits compressed image data to the work station 13. However, performance of the transmission may be influenced due to particular environment in the transmission, the position of the human body 10 or other factors. In view of this, a total size of data in the communication can be evaluated periodically for check. A ratio of image compression in the receiver 12 may be varied suitably according to the status in the wireless transmission between the receiver 12 and the workstation 13. If the performance of the transmission is found to be high, the total size of data per one image can be set high to keep the image quality high. This is advantageous in raising the precision in detecting necessary frame images. Furthermore, still higher performance in the transmission will make it unnecessary to compress image data in the receiver 12. There will be no need of selection of images in the processor 20, transmission of image selection information of necessary frame images to the receiver 12, or transmission of original images from the receiver 12 to the processor 20.

In contrast, it is possible to control in a frame memory of the receiver 12 to increase an image number of compressed image data to be written in a temporary manner when the performance of transmission becomes equal to or less than a reference standard level, so as to transmit information later by determining a lower limit in the suppression of a data size per one image to maintain the lowest sufficient image quality. Thus, it is possible to control a task suitably according to the performance of wireless transmission between the receiver 12 and the workstation 13.

Figure 8:
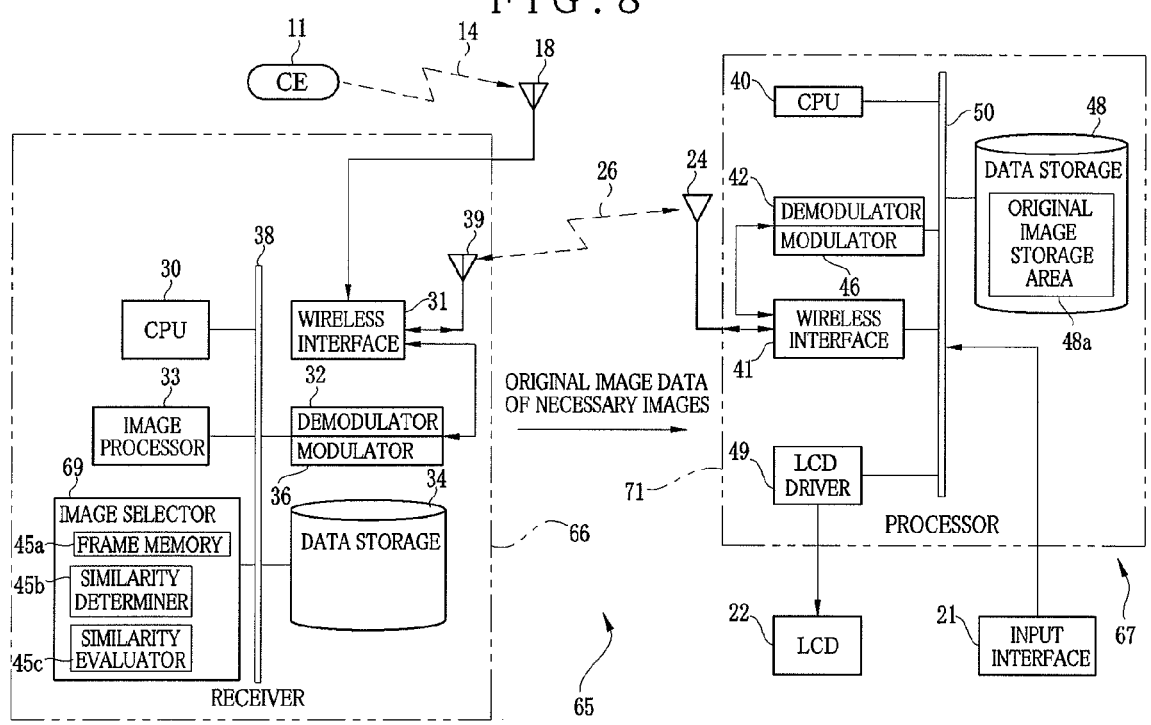
FIG. 8 is a block diagram illustrating circuit elements in a fourth preferred capsule endoscope system.
Figure 9:
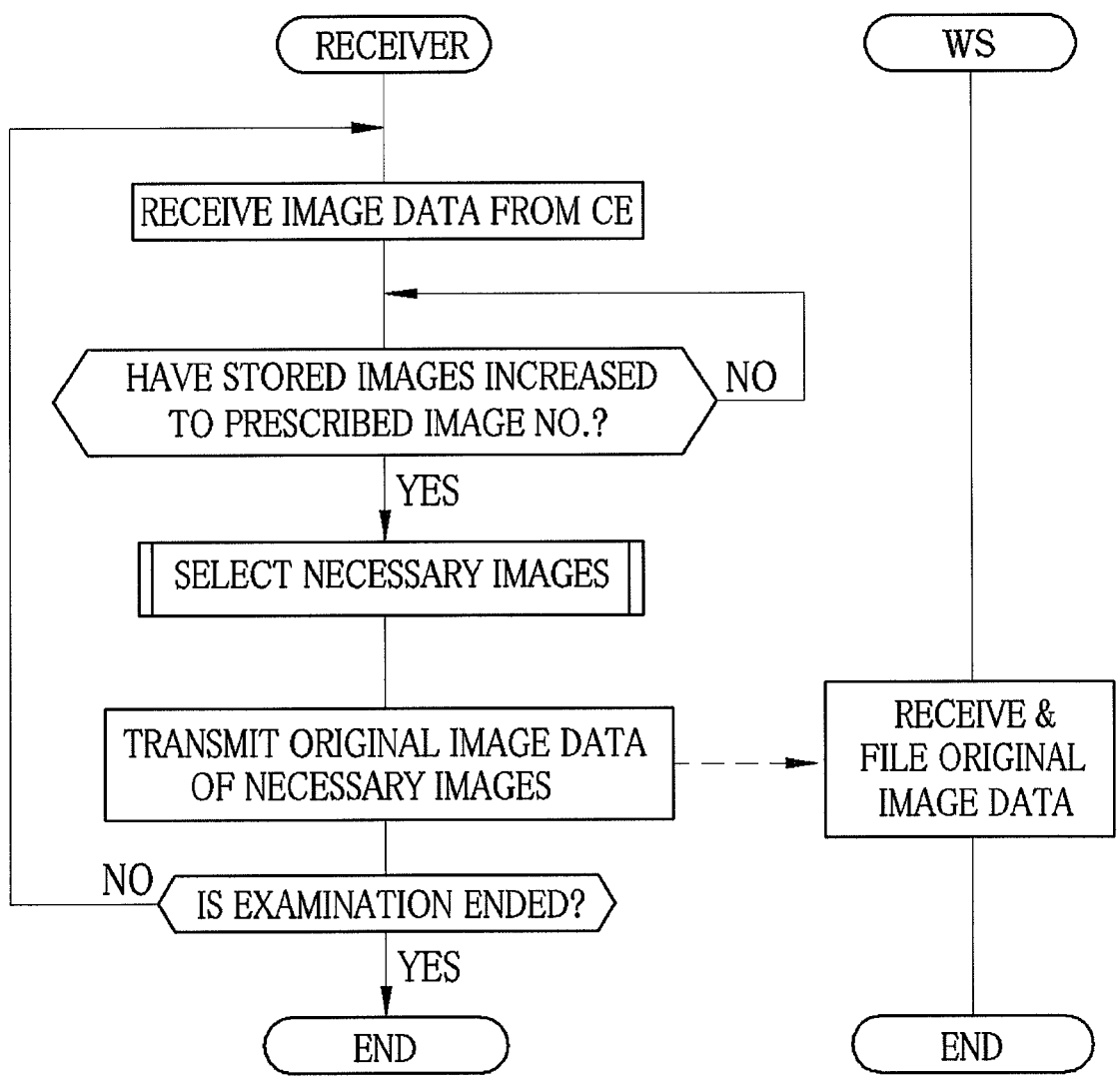
FIG. 9 is a flowchart illustrating transmission of original image data from a receiver to a workstation of the embodiment of FIG. 8.

A further preferred embodiment is described now. In a receiver, a selecting operation is carried out for necessary frame images unlike the above embodiments. In FIGS. 8 and 9, a capsule endoscope system 65 for this purpose is illustrated.

The capsule endoscope system 65 is constituted by the capsule endoscope 11, a receiver 66 and a workstation 67 for image filing. The receiver 66 is constructed equally to the receiver 12. An image selector 69 is incorporated in the receiver 66. Original image data, having transmitted from the capsule endoscope 11 to the antennas 18, the wireless interface 31, the demodulator 32 and the image processor 33, is written by the CPU 30 to a selection image memory (not shown).

The image selector 69 is constructed by repeating the image selector 45. Furthermore, when original image data of images of a predetermined image number are stored in the selection image memory, the image selector 69 selects necessary frame images among images of stored original image data. For the selecting operation, the "original image data" is read in place of the portion of "compressed image data" in the selecting operation of the embodiment of FIG. 3.

The CPU 30 writes original image data successively to a transmitting image memory (not shown) after being found to be necessary frame images by the image selector 69. When selection of all of the images is completed, the CPU 30 outputs original image data of necessary frame images to the modulator 36 from the transmitting image memory. The original image data of the necessary frame images are modulated into the radio wave 26, which is emitted by the antenna 39. Thus, the original image data of the necessary frame images are wirelessly transmitted from the receiver 66 to the workstation 67. Note that original image data found to be unnecessary frame images are abandoned by the CPU 30, or compressed and written to the data storage 34 by the CPU 30.

The workstation 67 includes a processor 71, the input interface 21 and the LCD display panel 22. The processor 71 is constructed by repeating the processor 20 or 55 but with a difference of not having an image selector. The radio wave 26 transmitted wirelessly by the receiver 66 is received by the antenna 24, and is demodulated by the processor 71 to provide original image data of images of a predetermined image number. The original image data are stored in a receiving image memory by one frame. The CPU 40 outputs all of original image data stored in the transmission image memory to the data storage 48, and written to the original image storage area 48a.

It is possible in the present fourth embodiment wirelessly to transmit only original image data of necessary images selected by the receiver 66 to the workstation 67 during the imaging with the capsule endoscope 11. The same effect as that of the first embodiment can be obtained even with a difference of having the image selector in the receiver 66. It is unnecessary in the present embodiment wirelessly to transmit compressed image data in the manner of the first embodiment, so that power for use in the transmission in the receiver can be reduced.

In the present embodiment, the image selector 69 constructed equally to the image selector 45 is incorporated in the receiver 66 for the selecting operation. However, a receiver may have the image selector 56 according to the second or third preferred embodiment.

In the above embodiment, the receiver transmits only original image data of necessary frame images. Furthermore, it is possible for the receiver to transmit all of the input original image data wirelessly to the workstation without selection of necessary and unnecessary frame images. To this end, the receiver can amplify an output of the wireless transmission (wireless power amplification) when the original image data from the capsule endoscope 11 are stored in the RAM or the like sufficiently in the predetermined image number, so as to transmit the original image data at one time wirelessly to the workstation.

In the above embodiments, the antenna 24 of FIG. 1B in connection with the workstation is attached to the ceiling 23 of the examination room. However, the antenna 24 may be installed in a certain position as desired. Also, a plurality of the antennas 24 may be disposed in the examination room and can be connected with the processor. A hospital may have a plurality of examination rooms. Each of the examination rooms can have an antenna which can be connected with one processor. Also, the workstation may be installed in an examination room. An antenna may be provided in a processor of the workstation. Furthermore, a plurality of the antennas 24 may be disposed at various points in the hospital or medical facilities, so that a space of a patient for moving can be enlarged with a much smaller limit.

In the first and second embodiments, a preceding image is determined as a necessary frame image and a succeeding image is determined as an unnecessary frame image in an image sequence when high similarity degree is found in the images in the frame memory 45a in the selecting operation for necessary frame images. However, a preceding image can be determined as an unnecessary frame image, and a succeeding image can be determined as an necessary frame image in an image sequence.

In the third embodiment, the image feature value extracted from the compressed image data is compared with the sample image feature value extracted previously from the sample image data, to evaluate similarity between the compressed image data and the sample image data. However, other methods of evaluating similarity may be used in the invention.

In the first, second and third embodiments, only original image data of necessary frame images are wirelessly transmitted from the receiver 12 to the workstation. However, the invention is not limited to those embodiments. For example, compressed image data may be data after lossless compression (compression encoding) of original image data in the receiver 12 or the image compressor 35. For this data, a decoder can be incorporated in the workstation for converting compressed image data of necessary frame images into original image data. It is unnecessary to send the original image data from the receiver 12 to the workstation, remarkably to decrease power for use in the transmission in the receiver. Also, only the original image data of necessary frame images can be written to the original image storage area 48a in a short time, because it is unnecessary to transmit image selection information from the workstation to the receiver, and to transmit original image data of necessary frame images from the receiver to the workstation.

In the above embodiments, the compression encoding is used to reduce the data size in the receiver 12. However, other methods may be used for data reduction, for example, frame thinning, pixel thinning and the like. Furthermore, the compression encoding, frame thinning and pixel thinning may be combined for use together.

The frame thinning of images is to reduce the number of images of original image data to reduce a size of data. For example, original image data of successive images recorded at 2 fps are thinned for one frame per K frames (K is an integer of 2 or more), and are stored in a transmission image memory. Note that, in case of the frame thinning in the image compressor 35, the image selector 45 of FIG. 2 selects one of images with the highest closeness to a preceding image as a succeeding image in the course of evaluating similarity between the preceding and succeeding images. If only the frame thinning is carried out for data reduction, it is possible to store only original image data selected by the image selector in the data storage 48. No transmission of original image data of necessary image frames from the receiver to the workstation is required.

The pixel thinning is a process of thinning the pixel number of pixels in original image data to reduce the data size. For example, pixels may be thinned in the vertical or horizontal direction in the original image data at a certain interval, which can be determined suitably for the purpose.

In the third embodiment, the feature value storage area 58 of FIG. 6 stores plural sample image data of various lesions. However, it is possible to store sample image feature values of plural sample image data according to various body parts in a human body in addition to various lesions. To this end, information of a body part and type of lesion for examination is input by use of the input keypad 21*a*, compressed image data with similarity to sample image data according to the input body part and type of lesion can be selected as compressed image data of necessary frame images.

The image selector and the feature value storage area are not limited to the above embodiments. For example, each one of the receiver and the workstation can include an image selector and a feature value storage area. For this structure, a selection switch can be added and used for selecting a desired one of the two image selectors in the receiver and the workstation.

In the above embodiment, the body for examination is a human body of a patient. However, a body of an animal other than the human being may be examined by use of the capsule endoscope of the invention.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A capsule endoscope system comprising:
a capsule endoscope, swallowable in a body, for forming an image in said body;
a receiver, positioned on said body, for wirelessly receiving said image from said capsule endoscope, to store said image;
an information manager for filing said image from said receiver, managing said image, and controlling display of said image;
a first wireless interface, positioned on said receiver, for wirelessly transmitting said image during imaging with said capsule endoscope;
a second wireless interface, positioned on said information manager, for wirelessly receiving said image from said first wireless interface;
an image selector for selecting said image for image filing in said information manager among plural images received by said receiver;
wherein said first wireless interface transmits said selected image to said information manager;
wherein said image selector is positioned on at least one of said receiver and said information manager; and
further comprising a memory, provided in one of said receiver and said information manager provided with said image selector, for storing a sample image feature value of a sample image;
said image selector extracts an image feature value from said image obtained by said capsule endoscope, and determines similarity degree between said image and said sample image by comparing said image feature value with said sample image feature value, wherein if said similarity degree is equal to or more than a predetermined threshold value, said image is selected as detected to correspond to said sample image, wherein said memory stores said sample image feature value in association with lesion type information of a type of a lesion;
further comprising an input interface for inputting said lesion type information;
said image selector reads said sample image feature value for comparison according to said input lesion type information.

2. A capsule endoscope system as defined in claim 1, wherein said image selector determines similarity degree between two images among plural images received from said capsule endoscope by said receiver, and if said similarity degree is equal to or more than a predetermined threshold value, selects one of said two images, and if said similarity degree is less than said threshold value, selects said two images.

3. A capsule endoscope system as defined in claim 1, wherein said image selector is positioned on said receiver.

4. A capsule endoscope system as defined in claim 1, wherein said image selector is positioned on said information manager.

5. A capsule endoscope system as defined in claim 4, wherein said receiver includes a data size reduction device for reducing a data size of said image received from said capsule endoscope before transmission in said first wireless interface.

6. A capsule endoscope system as defined in claim 4, wherein said second wireless interface transmits image selection information output by said image selector to said receiver;
said receiver designates said image according to said image selection information from said second wireless interface, and transmits said designated image with said first wireless interface.

7. A capsule endoscope system as defined in claim 6, wherein when there is a remaining image unselected with said image selector, said receiver abandons said remaining image or stores said remaining image in a modified form with a reduced size of data.

8. An endoscopic image filing method of filing an image formed in a body with a capsule endoscope swallowed in said body, comprising steps of:
wirelessly receiving said image from said capsule endoscope to a receiver positioned on said body, to store said image;
wirelessly transmitting said image from said receiver during imaging with said capsule endoscope;
filing said image wirelessly transmitted from said receiver;
further comprising selecting said image for image filing in said filing step among plural images received by said receiver;
wherein in said transmitting step, said selected image is transmitted, wherein a sample image feature value of a sample image is predetermined;
said selecting step includes:
extracting an image feature value from said image obtained by said capsule endoscope;
determining similarity degree between said image and said sample image by comparing said image feature value with said sample image feature value, wherein if said similarity degree is equal to or more than a predetermined threshold value, said image is selected as detected to correspond to said sample image, wherein said sample image feature value is predetermined in association with lesion type information of a type of a lesion; and
further comprising a step of inputting said lesion type information; and in said selecting step, said sample image feature value is read for comparison according to said input lesion type information.

9. An endoscopic image filing method as defined in claim 8, wherein in said selecting step, similarity degree between two images is determined among plural images received from said capsule endoscope by said receiver, and if said similarity degree is equal to or more than a predetermined threshold value, one of said two images is selected, and if said similarity degree is less than said threshold value, said two images are selected.

10. An endoscopic image filing method as defined in claim 8, further comprising a step of reducing a data size of said image received from said capsule endoscope to said receiver before said transmitting step.

11. An endoscopic image filing method as defined in claim 8, further comprising an information transmitting step of transmitting image selection information output by said selecting step to said receiver;

said receiver designates said image according to said image selection information from said information transmitting step, and transmits said designated image in said transmitting step.

12. An endoscopic image filing method as defined in claim 11, wherein when there is a remaining image unselected with said selecting step, said receiver abandons said remaining image or stores said remaining image in a modified form with a reduced size of data.

* * * * *